United States Patent [19]

Spence

[11] 4,019,209
[45] Apr. 26, 1977

[54] ARTIFICIAL BREAST FORM AND METHOD OF FORMING

[75] Inventor: Wayman R. Spence, Waco, Tex.

[73] Assignee: Spenco Medical Corporation, Waco, Tex.

[22] Filed: Apr. 22, 1976

[21] Appl. No.: 679,176

[52] U.S. Cl. .................................. 3/36; 128/479; 128/481; 264/130; 264/DIG. 30; 29/458; 29/527.2

[51] Int. Cl.² ...................... A61F 1/24; A41C 3/10

[58] Field of Search ......... 3/36; 128/462, 478–481, 128/DIG. 21; 2/267; 264/130, 222, DIG. 30; 29/458, 527.2

[56] References Cited

UNITED STATES PATENTS

| | | | |
|---|---|---|---|
| 3,067,431 | 12/1962 | Kausch | 3/36 |
| 3,494,365 | 2/1970 | Beals | 3/36 X |
| 3,665,520 | 5/1972 | Perras et al. | 3/36 |
| 3,896,506 | 7/1975 | Hankin et al. | 3/36 |

FOREIGN PATENTS OR APPLICATIONS 2,094,826  2/1972  France .................................. 3/36

Primary Examiner—Ronald L. Frinks
Attorney, Agent, or Firm—Richards, Harris & Medlock

[57] ABSTRACT

An artificial breast form to be worn externally on the body of a woman, not implanted in the body, constructed from preformed, self-contained, stable gel structure of breast compatible size and shape and covered with a porous elastic fabric cover which does not normally constrain the gel.

12 Claims, 3 Drawing Figures

ARTIFICIAL BREAST FORM AND METHOD OF FORMING

BACKGROUND OF THE INVENTION

Approximately one in fifteen women in the United States can currently be expected to develop breast cancer. The majority of these cancer patients require surgical removal of the breast and underlying muscular tissue, i.e., mastectomy and radical mastectomy, respectively. Following mastectomy, there is a need for an artificial breast form, not only for cosmetic and psychological benefit, but to balance the weight and feel of the normal breast on the chest, shoulders and back.

Further, many women have very small breasts and wear a variety of padded brassieres and synthetic breast forms to increase the appearance of the size of their breasts.

Artificial breast forms have heretofore been constructed of lightweight padding (fabrics and foams) or air-filled containers. Such breast forms have the disadvantages that they ride up in a brassiere to form an uneven appearance, they do not balance the weight of the normal breast, and they lack the feel and consistency of normal breasts.

Recognizing the importance of a weighted artificial breast form, prior breast forms have been filled with heavy, solid materials such as metal or sand or with liquids such as water or a variety of viscous fluids or with gels varying from starch gels to silicone gels.

Weighted breast forms, particularly those fluid-filled and gel-filled forms, have produced an improvement in weight, movement and feel of the artificial forms, but they all have had the disadvantage that they tend to collapse when the wearer reclines. Further, they leak when accidentally punctured. In addition, previously developed breast forms have been covered with impermeable membranes which have acted as containers for the inner core substance. Such membranes, because they are impermeable to air and liquid, have been made from rubber or plastic materials. Impermeable membranes covering artificial breast forms have the disadvantages that they trap heat and perspiration when placed against the chest, they have the feel of rubber or plastic, which is not a lifelike quality, and because the membranes must contain the inner core, they are relatively inelastic and thus unlike human skin.

SUMMARY OF THIS INVENTION

The present invention consists of an artificial breast form constructed with a preformed, self-contained gel covered with a porous, elastic or stretchable outer covering which does not contain the gel, but which functions only to provide a cosmetically-pleasing colored external surface and to reduce stickiness of the gel as it is handled or worn. Because the inner core of gel is preformed and self-contained by its own internal hydrostatic properties, puncture wounds (such as pinpricks) will have no appreciable effect on the gel core. Likewise, because the outer covering is porous, elastic and netlike, pin sticks will have no appreciable effect upon this part of the artificial breast form.

The novel features believed characteristic of the invention are set forth in the appended claims. The invention itself, however, as well as further objects and advantages thereof, will best be understood by reference to the following detailed description of an illustrative embodiment taken in conjunction with the accompanying drawings, in which:

Figure 1:
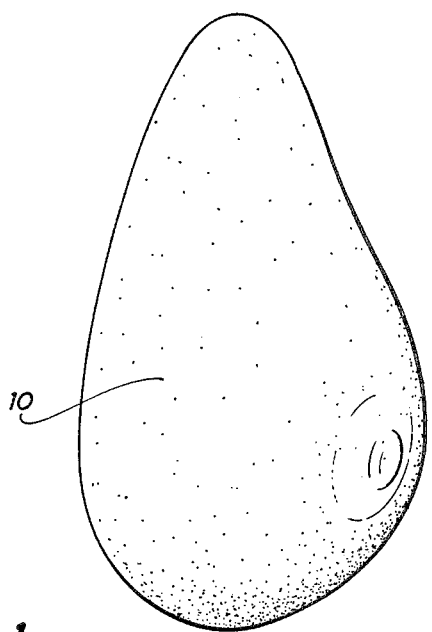
FIG. 1 is a perspective view of the artificial breast form embodying the present invention.
Figure 2:
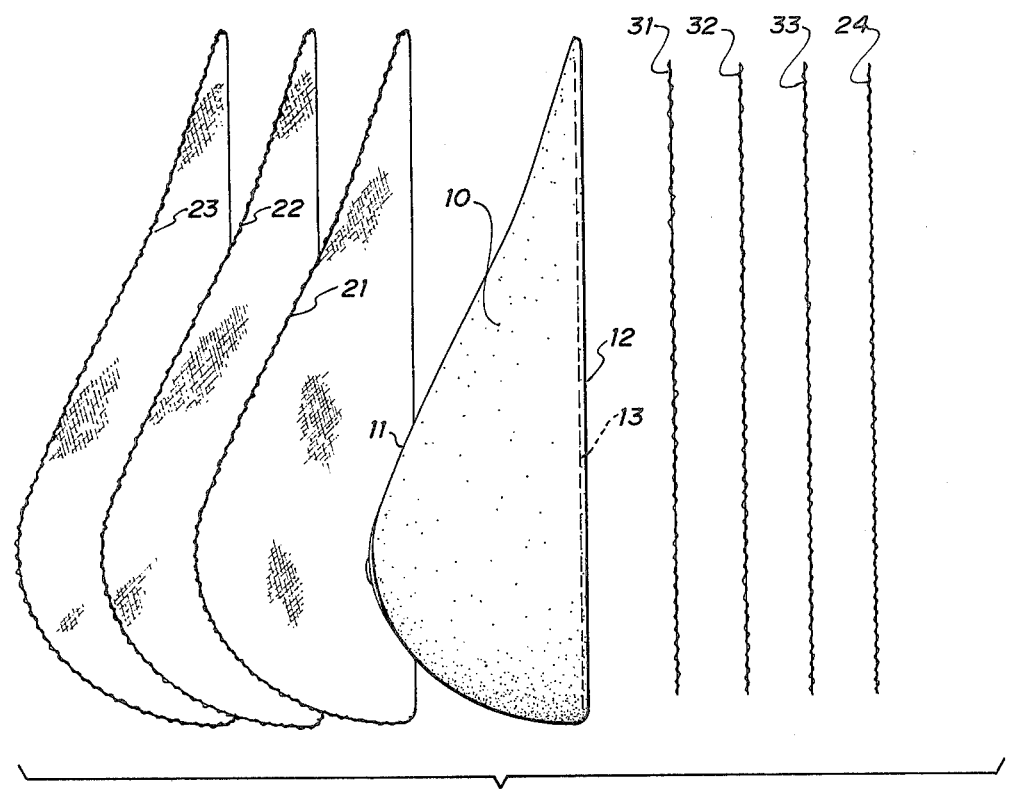
FIG. 2 is a vertical exploded view partially in section of the breast form of FIG. 1 and its cover.

Referring now to FIGS. 1 and 2, a breast form is illustrated of the type to be used by a woman following a mastectomy. A body of a silicone gel is formed to have the contour on the surface 11 conforming to the human female breast with what may be a substantially planar back surface 12. The gel 10 in a preferred form is a dielectric silicone gel of the type manufactured and sold by Dow Chemical Company of Midland, Mich., General Electric Company of Schenectady, N.Y. and others. The silicone gel preferably is a product of a reaction product of methyl polysiloxane containing silicone-bonded vinyl groups and a methyl polysiloxane containing SiH groups in which the reaction is catalyzed by platinum. When so catalyzed with the gel in a mold having the desired shape, the cured product results in a free standing self-contained body 10 which will closely approximate the form, density and pliability of a human female breast.

Such a self-contained gel preform normally has an extremely sticky surface. In accordance with the present invention, the preformed body 10 is thoroughly coated with a talcum or other suitable powder to eliminate the sticky character of the surface.

In a preferred embodiment, a layer 13 of a porous elastic stretchable fabric is impregnated with the gel and placed parallel to the rear surface 12, closely adjacent the surface and is thus integrally incorporated into the preform 10.

Completion of the artificial breast form in accordance with the present invention then involves application thereto of a plurality of layers of the porous elastic stretchable outer covering layers. As shown in FIG. 2, three layers 21, 22 and 23 are placed over the front surface 11 and layers 31, 32, and 33 are placed over the rear surface 12. Preferably they are edge stitched to the embedded layer 13. Finally, a back layer 24 is secured as by edge stitching to the back surface 12. The layer 24 may be any material known to be peculiarly suitable for wearing against human skin. Layer 24 may be eliminated in which case the rear surface would be the layer 33.

The preform 10 can be of any size and shape desired so that when worn by a person having had a mastectomy, symmetry and balance is restored to the form.

The preform 10, a self-contained gel body possesses hydrostatic properties such that the gel is capable of easily flowing laterally under pressure, but has a "memory" capable of returning to its original shape as a result of its internal restoring forces when the external pressure is removed. This same phenomenon is a characteristic of human breast tissue. When an external force, such as a hand, is pressed against breast tissue, the breast moves laterally in all directions. When the force is removed, the breast always returns to its precise original shape.

A variety of gels possess the ability to be displaced with a force exceeding gravity, and the ability to always return to their original shape when the force is removed. Silicone gels and vinyl gels are particularly adaptable to this characteristic. Silicone gels are particularly adaptable for artificial breast prostheses because they are very sticky and a fine fracture line produced by excessive pressure upon the gel will mend itself as the two fractured portions of the gel again stick together when the external force is removed.

An elastic, nonfriable, nonporous, chemically inert, semi-solid gel of a synthetic organic material which will resist bacterial and fungal growth and be stable over a large temperature range (−20 C to 65° C), is preferable. These properties are all contained by the silicone gels. The silicone gel used preferably is a product of a reaction product of a methyl polysiloxane containing silicone-bonded vinyl groups and a methyl polysiloxane containing SiH groups in which said reaction is catalyzed by platinum. This particular gel has a wide range of resistance to change with temperature and will not support bacterial growth and is hypoallergenic to the human body and chemically inert. This particular gel will not noticeably harden or become friable even after years of existence.

The gel core is preformed to the desired shape and particular breast size before it is covered. Once this gel core is formed into shape, pin sticks will not cause appreciable damage to the gel core. Because the preferred silicone gel core is quite sticky, however, it is desirable to create a non-sticky external surface by powdering the gel, such as with talcum or similar powder. The porous, elastic, net-like cover further functions to decrease the stickiness of the external surface of the gel core. The covering is porous, and sufficiently elastic or stretchable to avoid confining the original shape of the gel and any change in shape the gel must make when external forces are exerted upon it during normal use as an artificial breast form.

In contrast to the present invention, use of impermeable external coverings as in prior art products operates such that the gel is actually not self-contained. In such cases normal internal flow of the gel in response to pressures will be impeded and the structure will not feel like normal, human breast tissue. Furthermore, when an impermeable membrane is employed, it has been found that any puncture wound in the confining membrane will result in the gel exuding from the cut or punctured surface. In the present invention, such exuding will not take place because the covering is a net-like, porous, elastic, non-confining surface.

An additional feature of the porous, net-like, elastic, non-confining cover is that the cover has the ability to retain dyes for coloring. In this way, the breast form may be dyed with a wide variety of dyes, or its color may be changed with standard cosmetics or tinted body powders as the woman wearer may desire to change the external color of the breast prosthesis subtly to her own skin tones.

A two-way stretch nylon fabric placed in two or more layers over the inner sticky gel core, will function to provide all the features listed above for the porous, non-confining, elastic net-like cover.

As above noted, the same porous, woven fabric backing is impregnated into the posterior portion of the preformed, self-contained gel core as it is catalyzed into shape. This backing is placed at the posterior-most portion of the gel core before the core is gelled, so that the gel may impregnate the porous backing. The impregnated fabric not only strengthens the rear contour or surface of the gel core but provides a structure to anchor the elastic, porous, non-confining covering to the gel core itself. This leads to ease in manufacture, fitting the net-like covering over the gel form quickly and easily. The latter operations can be done with simple hand or machine sewing.

The artificial breast form comprising the inner gel core is always exposed to the external air and environment. It is a property of such a gel core that it will not coagulate, harden or become friable when exposed to the air. Exposure to air is ensured by the elastic, porous, net-like covering wich is very permeable to water and liquids. Further, puncture wounds, such as pins, which will cause artificial breast forms containing impermeable membranes to leak, will not cause leakage in the breast form in this invention.

Figure 3:
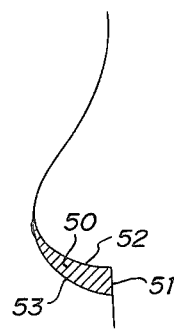
FIG. 3 illustrates the invention as embodied in an uplift pad.

Referring to FIG. 3, a modified form of structure is shown, particularly designed as an uplift pad 50 to be worn in a brassiere. It is shaped to be worn by one not to compensate for surgery but to enhance the appearance of the natural breast of the wearer. It has a rear surface 51 shaped to the contour of the chest below the breast. An upper cup shaped surface 52 contacts the under surface of the breast. The outer surface 53 is contoured to be consistent with the contour of the breast resting on surface 52.

Having described the invention in connection with certain specific embodiments thereof, it is to be understood that further modifications may now suggest themselves to those skilled in the art and it is intended to cover such modifications as fall within the scope of the appended claims.

What is claimed is:
1. An artificial breast form comprising:
   a. a preformed self-contained stabilized gel structure of breast size and shape, and
   b. a porous elastic fabric cover which yields in response to pressures exerted thereon by said gel.
2. The combination set forth in claim 1 in which said gel is a silicone gel, the reaction product of a methyl polysiloxane containing silicone-bonded vinyl groups and methyl polysiloxane containing SiH groups which has been catalyzed by platinum to establish and substantially retain said shape.
3. The combination set forth in claim 1 in which said gel is a dielectric silicone gel catalyzed to stably retain substantially said shape and coated with powder to avoid sticking to said cover.
4. The combination set forth in claim 1 in which a layer of a porous elastic fabric is impregnated with said gel and positioned as a subsurface layer beneath the posterior surface of said structure.
5. The combination set forth in claim 4 in which said porous elastic fabric cover is secured at the edges thereof to the edges of said impregnated layer.
6. The combination set forth in claim 4 in which said porous elastic fabric cover is stitched at the edges thereof to the edges of said impregnated layer.
7. The combination set forth in claim 1 in which said structure is powder coated to prevent sticking to said cover.
8. The combination set forth in claim 1 in which said structure is in the form of a complete breast to be used by a mastectomy patient.
9. The combination set forth in claim 1 in which said structure is in the form of an uplift pad to be worn in enhancement of a natural breast.
10. The method of forming a female breast form which comprises:
   a. impregnating a porous elastic fabric panel with a silicone and immersing said panel in the rear sur- face portion of a breast shaped body of said silicone as it is catalyzed to form a self-contained stabilized gel structure of breast size and shape, b. coating said structure with a powder to render the surfaces thereof nontacky, and c. applying over all surfaces of said structure a multi layer cover of a porous elastic fabric.

11. The method of claim 10 in which said cover is secured to said immersed fabric panel.

12. The method of claim 11 in which said cover is edged stitched to said immersed fabric panel.

* * * * *